United States Patent
Fang et al.

(10) Patent No.: US 7,241,937 B2
(45) Date of Patent: Jul. 10, 2007

(54) METHODS AND MATERIALS FOR IMPROVING PLANT DROUGHT TOLERANCE

(75) Inventors: Yiwen Fang, Los Angeles, CA (US); Roger I. Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/112,611

(22) Filed: Apr. 22, 2005

(65) Prior Publication Data

US 2006/0064785 A1 Mar. 23, 2006

Related U.S. Application Data

(60) Provisional application No. 60/565,028, filed on Apr. 23, 2004.

(51) Int. Cl.
| | |
|---|---|
| A01H 1/00 | (2006.01) |
| C07H 21/04 | (2006.01) |
| C12N 5/14 | (2006.01) |
| C12N 15/09 | (2006.01) |

(52) U.S. Cl. .................. 800/298; 435/468; 435/419; 435/320.1; 800/320.1; 536/23.1

(58) Field of Classification Search ................ None
See application file for complete search history.

(56) References Cited

U.S. PATENT DOCUMENTS

| | | | |
|---|---|---|---|
| 5,204,253 A | 4/1993 | Sanford et al. | |
| 5,538,880 A | 7/1996 | Lundquist et al. | |
| 5,591,616 A | 1/1997 | Hiei et al. | |
| 5,952,545 A | 9/1999 | Koncz et al. | |
| 6,329,571 B1 | 12/2001 | Hiei | |
| 2002/0104120 A1* | 8/2002 | Luchi et al. | 800/278 |
| 2003/0150026 A1 | 8/2003 | Chory et al. | |
| 2003/0199684 A1 | 10/2003 | Hirochika et al. | |

FOREIGN PATENT DOCUMENTS

| | | |
|---|---|---|
| EP | 1116794 A2 * | 7/2001 |
| WO | WO 200210210 A2 * | 2/2002 |
| WO | 2003/20015 | 3/2003 |

OTHER PUBLICATIONS

Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
GenBank Accession No. AAF26356.1, dated Jan. 19, 2000.
GenBank Accession No. AAK00623.1, dated Jun. 25, 2002.
GenBank Accession No. AAK00632.1, dated Jun. 25, 2002.
GenBank Accession No. AAK94454.1, dated Aug. 23, 2001.
GenBank Accession No. AAL07104.1, dated Sep. 18, 2002.
GenBank Accession No. BAB01336, dated Feb. 14, 2004.
GenBank Accession No. BAB11932.1, dated Dec. 1, 2000.
GenBank Accession NO. BAC10550.1, dated Aug. 21, 2002.
GenBank Accession No. BAC10551.1, dated Aug. 21, 2002.
GenBank Accession No. CAE02392.2, dated Jan. 16, 2006.
GenBank Accession No. NP_188062.1, dated Nov. 4, 2005.
GenBank Accession No. T04351, dated Nov. 6, 1997.
GenBank Accession No. T07123, dated Jun. 30, 1993.
GenBank Accession No. T51936, dated Feb. 6, 1995.
Bohnert et al., "Adaptions to Envirommental Stresses" 1995, *Plant Cell*, 7:1099-1111.
Bushell et al., "The Basis of Natural and Artificial Postzygotic Hybridization Barriers in *Arabidopsis* Species," *The Plant Cell*, 2003, 15:1430-1442.
Finkelstein et al., "Abscisic Acid Signaling in Seeds and Seedlings" *Plant Cell*, 2002, 14 Suppl:S15-S45.
Wang and Goodman, "An *Arabidopsis thaliana* root-specific kinase homolog is induced by dehydration, ABA, and NaCl" *Plant J.*, 1995, 8:37.
Hyrup et al., "Peptide Nucleic Acids (PNA): Synthesis, Properties and Potential Applications" *Bioorgan. Med. Chem.*, 1996, 4(1):5-23.
Jeddeloh et al., "Maintenance of genomic methylation requires a SW12/SNF2-like protein," *Nature Genetics*, 1999, 22:94-97.
Kakutani, "Genetic characterization of late-flowering traits induced by DNA hypomethylation mutation in *Arabidopsis thaliana*," *The Plant Journal*, 1997, 12(6):1447-1451.
Iuchi et al. "A Stress-Inducible Gene for 9-cis-Epoxycarotenoid Dioxygenase Involved in Abscisic Acid Biosynthesis under Water Stress in Drought-Tolerant Cowpea" *Plant Physiology*, 2000, 123:553-562.
Iuchi et al., "Regulation of drought tolerance by gene manipulation of 9-*cis*-epoxycarotenoid dioxygenase, a key enzyme in abscisic acid biosynthesis in *Arabidopsis*," *The Plant Journal*, 2001, 27(4):325-333.
Iuchi, Erratum re Iuchi et al. in *The Plant Journal*, 2001, 27(4):325-333, *The Plant Journal*, 2002, 30(5):611.
Qin and Zeevaart, "Overexpression of a 9-cix-Epoxycarotenoid Dioxygenase Gene in *Nicotiana plumbaginifolia* Increases Abscicic Acid and Phaseic Acid Levels and Enhances Drought Tolerance," *Plant Physiology*, 2002, 128:544-551.
Qin and Zeevaart, "The 9-*cis*-epoxycarotenoid cleavage reaction is the key regulatory step of abscisic acid biosynthesis in water-stressed bean," *PNAS*, 1999, 96(26):15354-15361.
Summerton and Weller, "Morpholino Antisense Oligomers: Design, Preparation, and Properties" *Antisense Nucleic Acid Drug Dev.*, 1997, 7(3):187-195.
Taylor et al., "Control of Abscisic acid synthesis," *J. Exp. Bot.* 51(350):1563-1574.
Thompson et al. "Abscisic acid biosynthesis in tomato: regulation of zeaxanthin epoxidase and 9-*cis*-epolxycarotenoid dioxygenase mRNAs by light/dark cycles, water stress and abscisic acid" *Plant Molecular Biology*, 2000, 42:833-845.
Thompson et al., "Ectopic expression of a tomato 9-*cis*-epoxycarotenoid dioxygenase gene causes over-production of abscisic acid," *The Plant Journal*, 2000, 23(3), 363-374.
Thompson et al., "CLUSTAL W: Improving the sensitivity of progressive multiple sequence alignment through sequence weighting, position-specific gap penalties and weight matrix choice" *Nucl. Acids Res.*, 1994, 22:4673-4680.
Xiong and Zhu, "Regulation of Abscisic Acid Biosynthesis" *Plant Physiol.*, 2003, 133:29-36.
Xiong et al., "Regulation of Osmotic Stress-responsive Gene Expression by the *LOS6ABA1*Locus in *Arabidopsis*," *The Journal of Biological Chemistry*, 2002, 277(10):8588-8596.

* cited by examiner (Continued)

Primary Examiner—Phuong Bui
Assistant Examiner—Vinod Kumar
(74) Attorney, Agent, or Firm—Fish & Richardson P.C.

(57) ABSTRACT

Isolated NCED3 nucleic acids and polypeptides are described herein, together with methods for using such nucleic acids and polypeptides for making transgenic plants with improved drought tolerance.

13 Claims, 5 Drawing Sheets

Figure 2A

ATGGCTTCTTTCACGGCAACGGCTGCGGTTTCTGGGAGATGGCTTGGTGGCGATCATATACTCAGCCGCCATTATCGTCTTCTCAAAGC
TCCGACTTGAGTTATTGTAGCTCCTTATGGCCCGGTCGTGTCACACGTAAGCTCAATGTTCATCGCCTTCATCTGCCTTCACACTCCTCCAG
CTCTTCATTCCCTAAGCAATCATCAAACTCTCCCGCCATTGTTGTTAAGCCAAAGCCAAAGAATCCAACAATAAACAGATGAATTG
TTCCAGAGAGGCGGGCGCAGCGTTGGACGCGGGAGGGTTCCTTGTCAGCCACGAAGCTACACCCGCTTCCTAAAACGG
CTGATCCTAGTGTTCAGATGCCGGGAAATTTGCTCCGGTGAATGAACAGCCCGTCCGGCGTAATCTTCCGGTGGTCGGAAAAATTC
CCGATTCCATCAAAGGAGTGTATGTGCCAACGGAGCTAACCCACTTCACGAGCCGGTCACCAGGTCACCACTCTTCGACGGAGAC
GGTATGGTTCACGCGCCGTCAAATTCGAAGACGGTTCAGCTACGCTTCACTCAGACTAACCGGTTTGTTCAGGAACGT
CAATTGGGTCGACCGGTTTCCCCAAAGCCATTCGGTGAGCTTCACGGACACACCGTATTGCCCGGCTCATGCTATTCTACGCCAGA
GCTGCAGCCGGTATAGTCGGCCCGGCAACCGGTGTGGCCAACGGTTTGGTCTATTTCAAGGCCGGTTATTGGCTAT
GTCGGAGGATGATTACCTTACCAAGTTCGATCACTCCCAATGGAAGATTTAAAAACCGTTCGGTCGTTCAATTTGATGGACAATTA
GAATCCACAATGATTGCCCACCCGAAATCACCCGGAATCACCGGTGAACTCTTCGCTTAAGCTACGACGTCGTTCAAAGCCTTAC
CTAAAATACTTCCGATTCTCACCGGACAAGTTCGTCGTACCTGACCAGCAAGTCGTTTCAAGCTGCCGGAGATCGCCGGGTCTCCGGTGTT
CGATTACAGAGAACAAGGTCGCAAGATTCGGGATTTTAGACAAATACGCCGAAGATTCATGCAACATTAAGTGGATTGATGCTCCAGATTG
ACGACAAGAACAAGGTCGCAAGATTCGGGAGAGCCTTGGGAAGAGCCAGAACAGATGAAGTCGTGATAGGTCCTGTATGACTCCACCAGACTC
CTTCGCTTCCATCTCTGGAACGCTTGGGAAGAGCCAGAACAGATGAAGTCGTGATAGGTCCTGTATGACTCCACCAGACTC
AATTTCAACGAGTCTGACGAGAATCAACAAGTCAACCTCGAAGCAGGAGTGTCCTGAATCTCAAAACGGTGAATCAACGGTGAATCAACCAATTCGCTTACT
ATCATCTCCAACGAAGATCAACAAGTCAACCTCGAAGCAGGATGGTCAACAGAAACGTCTTGGCCGTAAAACCAATTCGCTTACT
TGGCTTTAGCCGAGCCGGTGGCCGAGAGCCCTCTGTTTCTCCCCGGAGAAGGCCTTAGCGTTACGCCGTTAACGCGTTAAGCCGTTAAGAAACATCTTTACGGCGA
TAACCGTTAGCGGAGGAGAGCCCTCTGTTTCTCCCCGGAGAAGCAGGAGAAGAACGAAGGAATACATCCTCTGTTTCGTTCACGACGA
GAAGACATGGAAATCGGAGTTACAGATAGTTAACGCCGTTAACGCGTTAAGAGGTTGAAGCAACGGTTAAACTTCCGTCAAGGGTTCCGTAC
GGATTTCACGGTACATTCATCGGAGCCGATGATTTGGCGAAGCAGGTCGTGTGA (SEQ ID NO:1)

Figure 2B

MASFTATAAVSGRWLGGDHTQPPLSSSQSSDLSYCSSLPMAGRVTRKLNVSSALHTPPALHFPKQSSNSPAIVVKPKAKESNN
KQMNLFQRAAAAALDAAEGFLVSHEKLHPLPKTADPSVQIAGNFAPVNEQPVRRNLPVVGKIPDSIKGVYVRNGANPLHEPVTG
HHFFDGDGMVHAVKFEDGSASYACRFTQTNRFVQERQLGRPVFPKAIGELHGHTGIARLMLFYARAAAGIVGPAHGTGVANAG
LVYFNGRLLAMSEDDLPYQVRITPNGDLKTVGRFNFDGQLESTMIAHPKVDPESGELFALSYDVVSKPYLKYFRFSPDGTKSPD
VEIQLDQPTMMHDFAITENFVVVPDQQVVFKLPEMIRGGSPVVYDKNKVARFGILDKYAEDSSNIKWIDAPDCFCFHLWNAWEE
PETDEVVVIGSCMTPPDSIFNESDENLKGVLSEIRLNLKTGESTRRPIISNEDQQVNLEAGMVNRNVLGRKTKFAYLALAEPWPK
VSGFAKVDLTTGEVKKHLYGDNRYGGEPLFLPGEGGEEDEGYILCFVHDEKTWKSELQIVNAVSLEVEATVKLPSRVPYGFHGT
FIGADDLAKQVV (SEQ ID NO:2)

Figure 3

<2> MAT <10> TAAASNTWIGGNLP <4> PP <4> LSSSS <2> SSLLSYCSSS <1> S <1> SSTITRSLQVP <2> LHTP <1> ALQSPKQSS <6> TSPAIVVPTQAT <12> PSNS <5> KWNLFQRAAAALDAVEGALVSHEL EHP <2> LPKTADPRVQIAG <1> NFAPVPEHPVRQNLPVVGKIPKCIDGVYRNGANPLFEPVAGH HFFDGDGMVHAVKFTNGSASYACRFTETNRLVQERSLGRPVFPKAIGELHGHSGIARLMLFYA RGLFGLVDGSHGTGVANAGLVYFNGRLLAMSEDDLPYHVRITPNGDLKTVGRFDFDGQLEST MIAHPKLDPVSGELFALSYDVVQKPYLKYFRFSPDGTKSPDVEIPLDQPTMMHDFAITENFVVV PDQQVVFKLPEMIRGGSPVVYDKNKVSRFGILDKYAKDASEMKWIDAPDCFCFHLWNAWEEP ETDEVVVIGSCMTPPDSIFNESDESLKSVLSEIRLNLKTGESTRRPIISD <1> DEQVNLEAGMVN RNKLGRKTQFAYLALAEPWPKVSGFAKVDLTTGEVKKHLYGENRFGGEPLFLP <36> EGGEEDD G <1> YILA <9> FVHDEKTWKSELQIVNAVNLKLEAT <2> VKLPSRVPYGFHGTFI <1> A <1> DLA <1> Q
<15>

(SEQ ID NO:3)

METHODS AND MATERIALS FOR IMPROVING PLANT DROUGHT TOLERANCE

CROSS-REFERENCE TO RELATED APPLICATIONS

This application claims priority from U.S. Provisional Application Ser. No. 60/565,028, filed Apr. 23, 2004, which is incorporated herein by reference in its entirety.

FIELD OF THE INVENTION

The present invention relates to NCED3 nucleic acids and polypeptides, and to the use of those nucleic acids and polypeptides for making transgenic plants with improved drought tolerance.

BACKGROUND OF THE INVENTION

In the fields of agriculture and forestry, efforts have been made to produce plants with increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

In addition, plants are constantly exposed to a variety of biotic (e.g., pathogen infection and insect herbivory) and abiotic (e.g., high or low temperature, drought, and salinity) stresses. To survive these challenges, plants have developed elaborate mechanisms to perceive external signals and to manifest adaptive responses with proper physiological and morphological changes (Bohnert et al., 1995 *Plant Cell*, 7:1099–1111). Plants exposed to low water or drought conditions typically have low yields of plant material, seeds, fruit and other edible products. Some areas of the world consistently have very low rainfall and therefore have problems growing sufficient food crops for their population. Yet it has been observed that some plants survive and thrive in low water environments. To avoid reliance on breeding processes, it would be useful to identify genes that confer improved drought tolerance to enable the creation of transformed plants (such as crop plants) with improved drought tolerance characteristics.

SUMMARY OF THE INVENTION

This document relates to materials and methods for increasing the growth potential and drought tolerance in plants, characterized by expression of polynucleotides stably integrated into a plant genome. The document thus relates to isolated nucleic acids, polypeptides encoded thereby, and their inclusion in transgenic plants. The transgenic plants provided herein can have desired phenotypic characteristics relative to a control plant, such as improved drought tolerance. The present document also relates to plants having increased growth potential due to improved drought tolerance.

In one aspect, the invention features an isolated nucleic acid containing a nucleotide sequence that encodes a polypeptide having an amino acid sequence with at least 98.4 percent identity to the amino acid sequence set forth in SEQ ID NO:2. The isolated nucleic acid can further contain a control element operably linked to the nucleotide sequence encoding the polypeptide. The control element can be a broadly expressing promoter, a stress-inducible promoter, or a drought-inducible promoter. The isolated nucleic acid can further contain a selectable marker. The polypeptide can have an amino acid sequence with at least 98.7 percent identity, at least 99 percent identity, or at least 99.5 percent identity to the amino acid sequence set forth in SEQ ID NO:2.

In another aspect, the invention features a purified polypeptide having an amino acid sequence with at least 98.4 percent identity to the amino acid sequence set forth in SEQ ID NO:2. The polypeptide can have an amino acid sequence with at least 98.7 percent identity, at least 99 percent identity, or at least 99.5 percent identity to the amino acid sequence set forth in SEQ ID NO:2.

In another aspect, the invention features a transgenic plant containing at least one exogenous nucleic acid, the at least one exogenous nucleic acid containing a nucleotide sequence that encodes a polypeptide having an amino acid sequence with at least 98.4 percent identity to the amino acid sequence set forth in SEQ ID NO:2. The transgenic plant can exhibit a greater rate of growth under drought conditions relative to a corresponding plant of the same genetic background that lacks the nucleotide sequence encoding the polypeptide. The transgenic plant can exhibit enhanced drought-recovery relative to a corresponding plant of the same genetic background that lacks the nucleotide sequence encoding the polypeptide. The transgenic plant can exhibit a lower transpiration rate relative to a corresponding plant of the same genetic background that lacks the nucleotide sequence encoding the polypeptide. The at least one exogenous nucleic acid can encode a dicotyledonous 9-cis-epoxycarotenoid dioxygenase. The transgenic plant can be hemizygous or homozygous for the at least one exogenous nucleic acid. The transgenic plant can be an $F_1$ plant, $F_2$ plant, $BC_1$ plant, or $BC_2$ plant. The transgenic plant can be fertile. The transgenic plant can be dicotyledonous. The transgenic plant can be monocotyledonous (e.g., corn, wheat, rye, barley, oat, rice, millet, sorghum, Kentucky bluegrass, bluestem, weeping lovegrass, or fescue). The invention also features a seed of the transgenic plant described herein.

In another aspect, the invention features a method for producing a transgenic plant. The method can include (a) introducing at least one exogenous nucleic acid into a plant cell to produce a transformed plant cell, wherein the at least one exogenous nucleic acid contains a nucleotide sequence encoding a polypeptide with an amino acid sequence having at least 98.4 percent identity to the amino acid sequence set forth in SEQ ID NO:2, and (b) producing a transgenic plant from the transformed plant cell. The transgenic plant can exhibit a greater rate of growth under drought conditions relative to a corresponding plant of the same genetic background that lacks the nucleotide sequence encoding the polypeptide. The transgenic plant can exhibit enhanced drought-recovery relative to a corresponding plant of the same genetic background that lacks the nucleotide sequence encoding the polypeptide. The transgenic plant can exhibit a lower transpiration rate relative to a corresponding plant of the same genetic background that lacks the nucleotide sequence encoding the polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

BRIEF DESCRIPTION OF THE FIGURES

FIG. 2A sets forth the NCED3 cDNA sequence isolated from WS ecotype of *Arabidopsis thaliana* (SEQ ID NO:1). FIG. 2B sets forth the encoded NCED3 polypeptide sequence (SEQ ID NO:2).

FIG. 3 sets forth a consensus amino acid sequence (SEQ ID NO:3) for a 9-cis-epoxycarotenoid dioxygenase. The symbol "< >" indicates a variable number of amino acids. For example, <1> signifies that up to 1 (e.g., 0 or 1) amino acid of any type is permissible; <18> signifies that up to 18 (e.g., 0, 1, 2, 3, 4, 5, 6, 7, 8, 9, 10, 11, 12, 13, 14, 15, 16, 17, or 18) amino acids of any type are permissible.

DETAILED DESCRIPTION OF THE INVENTION

The plant hormone ABA is a sesquiterpenoid hormone that plays an important role in many physiological processes, including seed development and dormancy, vegetative growth, and responses to environmental stress. ABA levels increase when plants are subjected to drought, salt, or temperature stress, and these increased levels have been shown to be essential for stress tolerance (Xiong and Zhu (2003) *Plant Physiol.* 133:29–36). Modulation of ABA levels prior to the onset of stress also provides plants with better stress tolerance.

Figure 1:
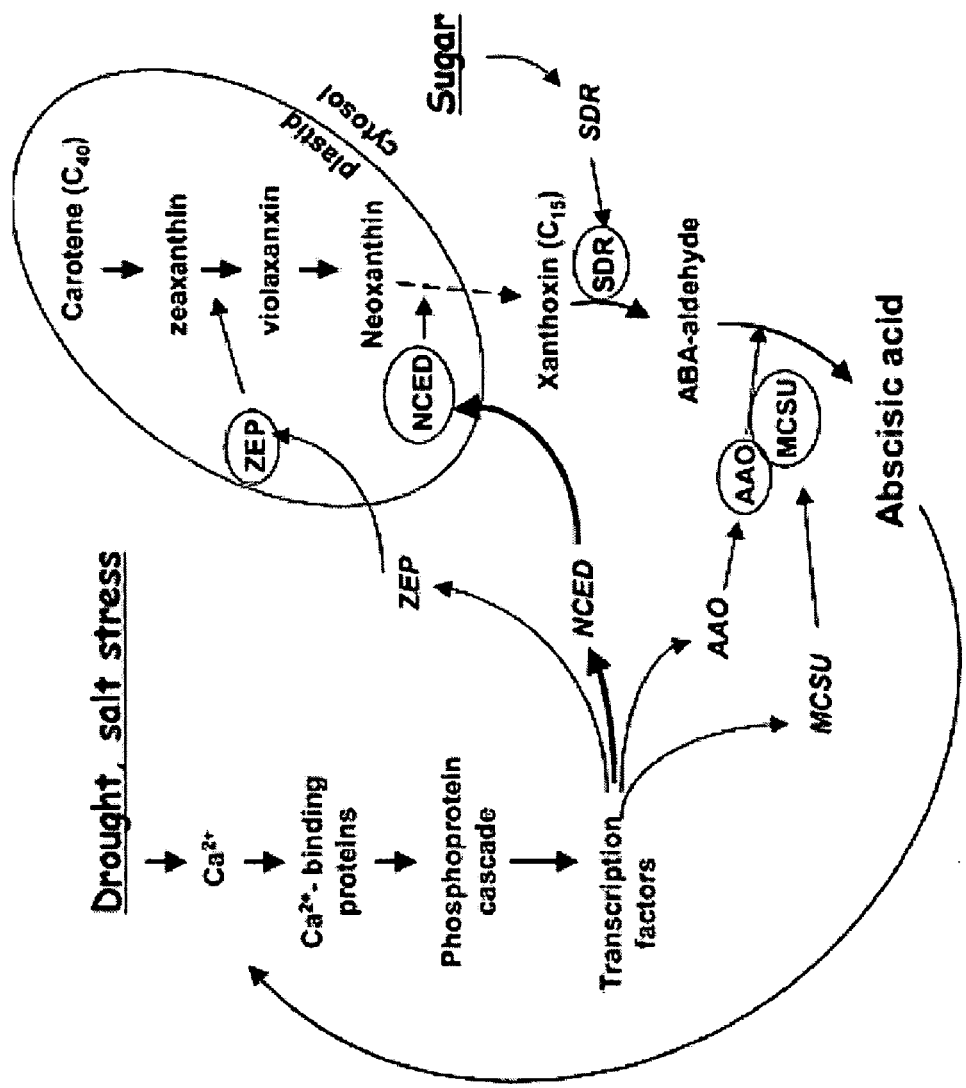
FIG. 1 is an illustration of ABA biosynthesis. NCED encodes a 9-cis-epoxycarotenoid dioxygenase that catalyzes production of xanthoxin, a key intermediate in ABA biosynthesis.

ABA is synthesized by the cleavage of a C40 carotenoid precursor followed by a two-step conversion of xanthoxin via an ABA-aldehyde (FIG. 1; Taylor et al. (2000) *J. Exp. Bot.* 51:1563–1574; and Finkelstein et al. (2002) *Plant Cell* 14 Suppl:S15–S45). Several *Arabidopsis* genes involved in ABA biosynthesis have been identified. One of these is NCED3, a gene encoding a 9-cis-epoxycarotenoid dioxygenase (NCED) that catalyzes production of xanthoxin, a key intermediate in ABA biosynthesis. As described herein, transgenic plants that overexpress NCED3 so that internal ABA levels are altered can better withstand stress (e.g., drought) conditions.

Polynucleotides and Polypeptides

Isolated NCED (e.g., NCED3) nucleic acids and polypeptides are provided herein. The terms "nucleic acid" or "polynucleotide" are used interchangeably herein, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. Nucleic acid analogs can be modified at the base moiety, sugar moiety, or phosphate backbone to improve, for example, stability, hybridization, or solubility of the nucleic acid. Modifications to the backbone can include the use of uncharged linkages (e.g., methyl phosphonates, phosphotriesters, phosphamidates, or carbamates) and charged linkages (e.g., phosphorothioates or phosphorodithioates). Modifications to the backbone also can incorporate peptidic linkages, e.g., to result in a PNA-type linkage. Modifications at the base moiety can include, for example, substitution of deoxyuridine for deoxythymidine and 5-methyl-2'-deoxycytidine or 5-bromo-2'-deoxycytidine for deoxycytidine. Modifications at the sugar moiety can include, for example, modification of the 2' hydroxyl of the ribose sugar to form 2'-O-methyl or 2'-O-allyl sugars. The deoxyribose phosphate backbone also can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7(3):187–195; and Hyrup et al. (1996) *Bioorgan. Med. Chem.* 4(1):5–23. In addition, the deoxyphosphate backbone can be replaced with, for example, a phosphorothioate or phosphorodithioate backbone, a phosphoroamidite, or an alkyl phosphotriester backbone.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

The term "polypeptide" as used herein refers to a compound of two or more subunit amino acids, amino acid analogs, or other peptidomimetics, regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers. Full-length proteins, analogs, mutants, and fragments thereof are encompassed by this definition.

By "isolated" or "purified" with respect to a polypeptide it is meant that the polypeptide is separated to some extent from the cellular components with which it is normally found in nature (e.g., other polypeptides, lipids, carbohydrates, and nucleic acids). An purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

When the polynucleotides and polypeptides provided herein are expressed non-naturally (e.g., with respect to location in a plant, such as root vs. stem; environmental condition; plant species; time of development; and/or in an increased or decreased amount), they can produce plants with an altered response(s) to drought conditions. These responses including for example, a greater rate of growth under drought conditions, enhanced drought-recovery, or lower transpiration rate, as evidenced by the transgenic plant analyses discussed herein. These traits can be used to make use of or maximize plant products. For example, nucleic acids provided herein can be used to generate transgenic plants having increased expression of one or more genes (e.g., NCED3) important for physiological plant performance during adverse environmental conditions. Such transgenic plants may require less water, leading to reduced costs for the farmer and better yield in drought conditions, as discussed herein. Thus, the polynucleotides and polypeptides provided herein can be useful in the preparation of transgenic plants having particular application in the agricultural and forestry industries.

Polynucleotides of the invention include nucleic acids that encode NCED polypeptides. SEQ ID NO:1 and SEQ ID NO:2, shown in FIGS. 2A and 2B, respectively, set forth Arabidopsis NCED3 polynucleotide and polypeptide sequences. SEQ ID NO: 3, shown in FIG. 3, sets forth a consensus NCED sequence. The present invention includes homologues and orthologs of these sequences, as well as proteins (and nucleotides encoding such proteins) that are functionally comparable to a polypeptide having the amino acid sequence shown in FIG. 2B or FIG. 3. Fragments, fusions, complements, and reverse complements of the described polynucleotides (and encoded polypeptides) also are contemplated.

Homologs and orthologs of a polypeptide also can be referred to as "functionally comparable" polypeptides. "Functionally comparable" polypeptides are polypeptides that have at least one characteristic in common. Such characteristics can include, for example, sequence similarity or identity, biochemical activity, transcription pattern, and phenotypic activity. For example, functionally comparable polypeptides that are have similar biochemical activity may be able to act on the same reactant to give the same product. Such "biochemically comparable" polypeptides may or may not exhibit the same kinetics, affinity for the reactant, or turnover time to produce the product, but can still be considered functionally comparable because the same end product is produced. For example, a functionally comparable polypeptide can exhibit at least 60% of the biochemical activity of a 9-cis-epoxycarotenoid dioxygenase protein having the amino acid sequence set forth in SEQ ID NO:2 or SEQ ID NO:3, e.g., at least 70%, 80%, 90%, or 95% of the biochemical activity. Methods for evaluating biochemical activities include those known to persons having ordinary skill in the art, and include, for example, enzymatic assays and radiotracer feeding assays.

Another class of functionally comparable polypeptides, referred to herein as "phenotypic comparables," can affect the same physical characteristic, such as plant size or height or metabolic profile. Polypeptides can be considered to be phenotypic comparables even if the polypeptides affect the same physical characteristic but to different degrees. For example, phenotypically comparable polypeptides can affect the same characteristic (e.g., to result in increased height) where the quantitative measurement due to one of the comparable polypeptides is about 20% or more of the other; e.g., about 20 to 30%; about 30 to 40%; about 40 to 50%; about 50 to 60%; about 60 to 70%; about 70 to 80%; about 80 to 90%; or about 90 to 100%. Thus, two polypeptides can be phenotypic comparables although one protein increases plant height by 10% and the other increases plant height by 15%.

A consensus NCED sequence amino acid sequence, such as that presented in FIG. 3, can be determined by aligning 9-cis epoxycarotenoid dioxygenase sequences from a variety of plant species and determining the most common amino acid or type of amino acid at each position. For example, a consensus sequence can be determined by aligning amino acid sequences from Arabidopsis NCED3 (GenBank accession no. BAB01336), avocado NCED3 (GenBank accession no. AAK00623.1), avocado 9-cis-epoxycarotenoid dioxygenase (GenBank accession no. AAK00632.1), Arabidopsis At3g14440 polypeptide sequence (GenBank accession no. NP_188062.1), Arabidopsis putative 9-cis-epoxycarotenoid dioxygenase (GenBank accession no. AAL07104.1), soybean putative 9-cis-epoxycarotenoid dioxygenase (Ceres clone no. 528092), bean 9-cis-epoxycarotenoid dioxygenase (GenBank accession no. AAF26356.1), pea NCED2 (GenBank accession no. BAC10550.1), pea NCED3 (GenBank accession no. BAC10551.1), cowpea neoxanthin cleavage enzyme (GenBank accession no. BAB11932.1), tomato 9-cis-epoxycarotenoid dioxygenase (GenBank accession no. T07123), potato probable 9-cis-epoxycarotenoid dioxygenase (GenBank accession no. T51936), lettuce 9-cis-epoxycarotenoid dioxygenase (GenBank accession no. AAK94454.1), wheat putative 9-cis epoxycarotenoid dioxygenase (Ceres clone no. 704111), corn viviparous-14 polypeptide (GenBank accession no. T04351), and rice polypeptide sequence from chromosome 4, BAC clone OSJNBb0080H08 (GenBank accession no. CAE02392.2). Such an alignment can be used to generate a consensus sequence such at that set forth in SEQ ID NO:3 (FIG. 3).

The isolated polypeptides provided herein can exhibit various levels of sequence identity to the NCED3 sequence set forth in SEQ ID NO:2 or the consensus NCED sequence set forth in SEQ ID NO:3. As described below, for example, an isolated nucleic acid can include a nucleotide sequence that encodes a polypeptide having an amino acid sequence with at least 90 percent identity to the NCED3 sequence set forth in FIG. 2B (SEQ ID NO:2), or to the consensus NCED sequence set forth in FIG. 3 (SEQ ID NO:3). Such polypeptides can be utilized, e.g., to make transgenic plants with a greater rate of growth under drought conditions, enhanced drought recovery, and/or lower transpiration rate.

The polypeptides provided herein can have amino acid sequences with at least 90% identity (e.g., 95%, 96%, 97%, 98%, 98.1%, 98.2%, 98.3%, 98.4%, 98.5%, 98.6%, 98.7%, 98.9%, 99.0%, 99.1%, 99.2%, 99.3%, 99.4, 99.5%, 99.6%, or 100% sequence identity) to the amino acid sequence set forth in SEQ ID NO:2 or SEQ ID NO:3. Similarly, the nucleic acids provided herein can have nucleotide sequences with at least 90% sequence identity (e.g., 95%, 96%, 97%, 98%, 98.1%, 98.2%, 98.3%, 98.4%, 98.5%, 98.6%, 98.7%, 98.9%, 99.0%, 99.1%, 99.2%, 99.3%, 99.4, 99.5%, 99.6%, or 100% sequence identity) to the nucleotide sequence set forth in SEQ ID NO:1. The sequence identity refers to the degree of identity between any given query sequence (e.g., an NCED3 sequence) and a subject sequence (e.g., the NCED3 sequence set forth in SEQ ID NO:2). The percent identity for any query nucleic acid or amino acid sequence relative to another subject nucleic acid or amino acid sequence is determined as follows.

A query nucleic acid or amino acid sequence is compared and aligned with one or more subject nucleic acid or amino acid sequence using the program ClustalW, which allows alignment of DNA and protein sequences across their entire length (global alignment). ClustalW calculates the best match for the selected sequences and lines them up so that the identities, similarities and differences can be examined (Thompson et al. (1994) *Nucl. Acids Res.* 22:4673–4680). Gaps of one or more residues can be inserted into a query or subject sequence to maximize sequence alignments. The result reflects the relationship between sequences. ClustalW can be run online, for example, at the Baylor College of Medicine Search Launcher site (searchlauncher.bcm.tmc.edu/multi-align/multi-align) and at the European Bioinformatics Institute site on the World Wide Web (ebi.ac.uk/clustalw), using ClustalW version 1.83, default parameters. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on.

To determine a percent identity between a query sequence and a subject sequence, the number of matching bases or amino acids is divided by the total number of bases or amino acids, and multiplied by 100. For example, if a query nucleotide sequence and a subject nucleotide sequence each are 500 base pairs long and have 200 matched (or identical) bases, these nucleotide sequences are 40 percent identical. If the two compared sequences are of different lengths, the number of matches is divided by the shorter of the two sequence lengths. For example, if 100 amino acids are matched between a 400 amino acid query polypeptide and a 500 amino acid subject polypeptide, these polypeptides would be 25 percent identical with respect to the query polypeptide.

It will be appreciated that a query nucleotide or amino acid sequence that aligns with a subject sequence can result in many different lengths, with each length having its own percent identity. In addition, it is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

A polypeptide provided herein can have the NCED3 amino acid sequence set forth in SEQ ID NO:2. Alternatively, a polypeptide can have the NCED3 amino acid sequence set forth in SEQ ID NO:2, with the proviso that the amino acid sequence of the polypeptide has a substitution relative to SEQ ID NO:2 at one to nine (e.g., 1, 2, 3, 4, 5, 6, 7, 8, or 9) positions selected from the group consisting of positions 18, 42, 83, 145, 184, 239, 271, 285, 447, and 485. For example, a polypeptide can have the amino acid sequence set forth in SEQ ID NO:2, with the proviso that the polypeptide has an asparagine at position 18, a serine at position 42, a threonine at position 83, a leucine at position 145, a histidine at position 184, an aspartic acid at position 239, a glutamine at position 271, an aspartic acid at position 285, a serine at position 447, or a methionine at position 485, or any combination thereof at up to nine positions of the disclosed group.

Recombinant Constructs, Vectors and Host Cells

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The terms "regulatory sequence," "control element," and "expression control sequence" refer to nucleotide sequences that influence transcription or translation initiation and rate, and stability and/or mobility of the transcript or polypeptide product. Regulatory sequences include, but are not limited to, promoters, promoter control elements, protein binding sequences, 5' and 3' untranslated regions (UTRs), transcriptional start sites, termination sequences, polyadenylation sequences, introns, and other regulatory sequences that reside within a coding sequence. As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into mRNA, which then can be translated into the protein encoded by the coding sequence.

A promoter is an expression control sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Promoters referred to as "constitutive promoters" can promote transcription under many, but not necessarily all, environmental conditions and states of development or cell differentiation. Non-limiting examples of constitutive promoters include the cauliflower mosaic virus (CaMV) 35S transcript initiation region and the 1' or 2' promoter derived from T-DNA of *Agrobacterium tumefaciens*, p32449, p13879, and other transcription initiation regions from various plant genes, such as the maize ubiquitin-1 promoter, known to those of skill in the art.

A promoter can be said to be "broadly expressing" when it promotes transcription in many, but not necessarily all, plant tissues. For example, a broadly expressing promoter can promote transcription of an operably linked sequence in one or more of the stem, shoot, shoot tip (apex), roots and leaves, but can promote transcription weakly or not at all in tissues such as reproductive tissues of flowers and developing seeds. A broadly expressing promoter operably linked to a coding sequence can promote transcription of the linked sequence in a plant shoot at a level that is at least two times (e.g., at least 3, 5, 10, or 20 times) greater than the level of transcription in developing seed, for example. Alternatively or in addition, a broadly expressing promoter can promote transcription in a plant shoot at a level that is at least two times (e.g., at least 3, 5, 10, or 20 times) greater than the level of transcription in a reproductive tissue of a flower. Examples of broadly expressing promoters include, without limitation, p326, YP0050, YP0144 and YP0190.

A "plant promoter" is a promoter capable of initiating (promoting) transcription in plant cells. Such promoters need not be of plant origin. For example, promoters derived from plant viruses, such as the CaMV 35S promoter, or from *Agrobacterium tumefaciens* such as the T-DNA promoters, can serve as plant promoters. An example of a plant promoter of plant origin is the maize ubiquitin-1 (ubi-1) promoter. Other suitable plant promoters include those known to persons of ordinary skill in the art. A plant promoter can direct expression of a nucleotide sequence in all or certain tissues of a plant, e.g., a constitutive promoter such as 35S or a broadly expressing promoter such as p326. Alternatively, a plant promoter can direct transcription of a nucleotide sequence in a specific tissue (tissue-specific promoters) or can be otherwise under more precise environmental control (inducible promoters).

An "inducible promoter" refers to a promoter that is regulated by particular conditions, such as light, anaerobic conditions, temperature, chemical concentration, protein concentration, conditions in an organism, cell, or organelle. Stress-inducible promoters, for example, can be activated under conditions of stress, such as drought, high or low temperature, lack of appropriate nutrients. One example of an inducible promoter that can be utilized with the polynucleotides provided herein is PARSK1. This promoter is from an *Arabidopsis* gene encoding a serine-threonine kinase enzyme, and is induced by dehydration, ABA, and sodium chloride (Wang and Goodman (1995) *Plant J.* 8:37). Other examples of stress-inducible promoters include PT0633 and PT0688. These promoters may be inducible under conditions of drought.

A polyadenylation region at the 3'-end of a coding region can also be operably linked to a NCED3 coding sequence. The polyadenylation region can be derived from the natural gene, from various other plant genes, or from Transfer-DNA (T-DNA).

The vectors provided herein also can include, for example, origins of replication, scaffold attachment regions (SARs), and/or markers. A marker gene can confer a selectable phenotype on a plant cell. For example, a marker can confer, biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The recombinant DNA constructs provided herein typically include a NCED polynucleotide sequence inserted into a vector suitable for transformation of plant cells. Recombinant vectors can be made using, for example, standard recombinant DNA techniques (see, e.g., Sambrook et al. (1989) *Molecular Cloning: A Laboratory Manual*, 2nd ed., Cold Spring Harbor Laboratory, Cold Spring Harbor, N.Y.).

Transgenic Plants

The vectors provided herein can be used to transform plant cells and generate transgenic plants. Thus, transgenic plants containing the nucleic acids described herein also are provided, as are methods for making such transgenic plants. Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880, 5,204,253, 5,591,616, and 6,329,571). If a cell or tissue culture is used as the recipient tissue for transformation, plants can be regenerated from transformed cultures using techniques known to those skilled in the art.

An "exogenous" nucleic acid refers to a polynucleotide that has been introduced into the genome of a host cell or an organism by recombinant DNA technology. An exogenous nucleic acid is not originally resident in the plant that is the recipient of the nucleic acid, but it is within the scope of the invention to introduce one or more copies of a nucleic acid into the same species of plant from which the nucleic acid was originally isolated. Typically, an exogenous polynucleotide is stably integrated into the genome of a host cell or organism.

A transgenic cell or plant containing an exogenous nucleic acid is referred to herein as an $R_1$ cell or plant for the primary transgenic cell or plant, an $R_2$ cell or plant for the first generation, and $R_3$, $R_4$, etc. for second and subsequent generation of cells or plants. $R_2$ refers to the progeny of the cell or plant of the $R_1$ generation. For example, an $R_2$ plant can be the result of self-fertilization of an $R_1$ plant. $R_3$ refers to the progeny of the cell or plant of the $R_2$ generation. For example, a $R_3$ plant refers to the second generation progeny of the cell or plant that is the direct result of a transformation experiment; an $R_3$ plant can be the result of self-fertilization of an $R_2$ plant. Transgenic plants can be entered into a breeding program, e.g., to introduce a nucleic acid into other lines, to transfer a nucleic acid to other species or for further selection of other desirable traits. Alternatively, transgenic plants can be propagated vegetatively for those species amenable to such techniques. Progeny can include descendants of a particular plant or plant line. For example, progeny can include seeds formed on $F_1$, $F_2$, $F_3$, $F_4$, $F_5$, $F_6$, $F_7$, $F_8$, $F_9$, and subsequent generation plants, or seeds formed on $BC_1$, $BC_2$, $BC_3$, $BC_4$, $BC_5$, $BC_6$ and subsequent backcross generation plants. Seeds produced by a transgenic plant can be grown and then selfed (or outcrossed and selfed) to obtain seeds homozygous for a nucleic acid encoding a novel polypeptide.

Ectopic expression of the nucleic acids provided herein can be accomplished using a "knock-in" approach. Here, the first component, an "activator line," is a transgenic plant containing a transcriptional activator operatively linked to a promoter. The second component contains the desired cDNA sequence operatively linked to the target binding sequence/region of the transcriptional activator. The second component is transformed into the "activator line" or is used to transform a host plant to produce a "target" line that is crossed with the "activator line" by ordinary breeding methods. In either case, the result is that the promoter drives production of the transcriptional activator protein, which then binds to the target binding region to facilitate expression of the desired cDNA.

Any promoter that functions in plants can be used in the first component, such as a constitutive promoter, a tissue or organ specific promoter, or a broadly expressing promoter. Inducible promoters can also be used, such as stress- (e.g., drought-) inducible promoters, ABA-inducible promoters, or low-humidity inducible promoters. Suitable transcriptional activator polypeptides include, without limitation, those encoding HAP1 and GAL4. The binding sequence recognized and targeted by the selected transcriptional activator protein is used in the second component.

Transformed plant cells can be cultured to regenerate a plant that possesses the transformed genotype. Regeneration techniques can rely on manipulation of phytohormones in tissue culture growth media, and may rely on a biocide and/or herbicide marker introduced with the polynucleotide of interest. Regeneration can also be obtained from plant protoplasts, callus, explants, organs, pollens, embryos, or parts thereof.

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. After a polynucleotide is stably incorporated into a transgenic plant, it can be introduced into other plants using, for example, standard breeding techniques.

The polynucleotides and vectors described herein can be used to transform a number of monocotyledonous and dicotyledonous plants and plant cell systems, including dicots such as safflower, alfalfa, soybean, coffee, rapeseed (high erucic acid and canola), or sunflower as well as monocots such as corn, wheat, rye, barley, oat, rice, millet, amaranth or sorghum. The polynucleotides and polypeptides provided herein can find particular application in the agricultural and forestry areas, and thus are useful in such crops as grain crops (e.g., wheat, maize, rice, millet, and barley); fruit crops (e.g., tomato, apple, pear, strawberry, orange, grape, strawberry, pineapple, melon (e.g., watermelon and cantaloupe), peach, pear, cherry, lemon, grapefruit, plum, mango, banana, and palm); forage crops (e.g., alfalfa); vegetable or root crops (e.g., carrot, potato, sugar beets, yams, onion, broccoli, peas, soybean, sweet corn, popcorn, tomato, potato, beans (including kidney beans, lima beans, dry beans, and green beans), lettuce, and spinach); flowering plants (e.g., petunia, rose, and chrysanthemum); conifers and pine trees (e.g., pine, fir, and spruce); oil crops (e.g., sunflower and rape seed); tobacco; plants used for experimental purposes (e.g., *Arabidopsis*); and native plants (e.g., guayule (*Parthenium argentatum*)).

Thus, the methods described herein can be utilized with dicotyledonous plants belonging to, without limitation, the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Methods described herein also can be utilitzed with monocotyledonous plants belonging to, without limitation, the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales, or with plants belonging to Gymnospermae, e.g., Pinales, Ginkgoales, Cycadales and Gnetales.

As such, the invention has use over a broad range of plant species, including species from, without limitation, the genera *Allium, Alseodaphne, Anacardium, Arachis, Asparagus, Atropa, Avena, Beilschmiedia, Brassica, Citrus, Citrullus, Capsicum, Catharanthus, Carthamus, Cocculus, Cocos, Coffea, Croton, Cucumis, Cucurbita, Daucus, Duguetia, Elaeis, Eschscholzia, Ficus, Fragaria, Glaucium, Glycine, Gossypium, Helianthus, Heterocallis, Hevea, Hordeum, Hyoscyamus, Lactuca, Landolphia, Linum, Litsea, Lolium, Lupinus, Lycopersicon, Malus, Manihot, Majorana, Medicago, Musa, Nicotiana, Olea, Oryza, Panicum, Panieum, Pannesetum, Papaver, Parthenium, Persea, Petunia, Phaseolus, Pinus, Pistachia, Pisum, Pyrus, Prunus, Raphanus, Rhizocarya, Ricinus, Secale, Senecio, Sinomenium, Sinapis, Solanum, Sorghum, Stephania, Theobroma, Trigonella, Triticum, Vicia, Vinca, Vitis, Vigna* and *Zea*.

Transgenic plants can exhibit any of the biochemical activities of the polypeptides described herein. For example, a transgenic plant can exhibit at least one of the biochemical activities of a 9-cis-epoxycarotenoid dioxygenase. Methods for evaluating biochemical activities are known to those having ordinary skill in the art.

The transgenic plants provided herein also can exhibit an enhanced response to adverse environmental conditions relative to corresponding control plants that either are not transgenic or that are transgenic for the NCED nucleic acid but do not express the NCED polypeptide. For example, transgenic plants can exhibit a greater rate of growth under drought conditions, or may exhibit enhanced drought-recovery capabilities in conditions that involve a drought period followed by re-hydration. Transgenic plants also can exhibit lower transpiration rates than corresponding control plants. Methods for evaluating altered physiological parameters such as plant height and plant transpiration rates are known to those having ordinary skill in the art, and also are discussed herein.

Transgenic plants can have an altered phenotype as compared to a corresponding control plant that either lacks the transgene or does not express the transgene. A polypeptide can affect the phenotype of a plant (e.g., a transgenic plant) when expressed in the plant, e.g., at the appropriate time(s), in the appropriate tissue(s), or at the appropriate expression levels. Phenotypic effects can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (i.e., where expression is under the control of an inducible promoter). A plant can be said "not to express" a polypeptide when the plant exhibits less than 10% (e.g., less than 9%, 8%, 7%, 6%, 5%, 4%, 3%, 2%, 1%, 0.5%, 0.1%, 0.01%, or 0.001%) of the amount of polypeptide or mRNA encoding the polypeptide exhibited by the plant of interest. Expression can be evaluated using methods including, for example, RT-PCR, Northern blots, S1 RNAse protection, primer extensions, Western blots, protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

A phenotypic effect can be an altered growth rate under a stressful environmental condition relative to a control plant. For example, a transgenic plant can exhibit a greater rate of growth under drought conditions. In another example, a transgenic plant can exhibit a greater rate of growth following re-hydration immediately preceded by drought. Thus, the physiological condition of a plant under drought conditions, or following drought and re-hydration treatments can be a measure of its drought-recovery capability, and can be assessed with physiological parameters such as, for example, plant height, number of new shoots, number of new leaves, or seed number.

When a polypeptide described herein is expressed in a transgenic plant, the transgenic plant can exhibit a height that is from about 7% to about 20% greater (e.g., about 10% to about 15%; about 12% to about 18%; about 8% to about 18%; or about 15% to about 20% greater) than a plant not expressing the polypeptide. In another example, when a polypeptide described herein is expressed in a transgenic plant, the transgenic plant can exhibit more new growth than a plant not expressing the polypeptide. New growth can be measured as the number of new shoots or new leaves on a plant. Thus, for example, a transgenic plant can have from 1 to 10 more (e.g., 1, 2, 3, 4, 5, 6, 7, 8, 9, or 10 more) new shoots, or even more than 10 more new shoots, than a corresponding control plant. In another example, when a polypeptide described herein is expressed in a transgenic plant, the transgenic plant can exhibit a greater number of new leaves following a drought or drought and re-hydration treatments, as compared to a plant not expressing the polypeptide. For example, a transgenic plant can have from 1 to 50 more (e.g., 2, 4, 6, 7, 8, 9, 10, 12, 15, 16, 18, 20, 25, 29, 30, 32, 35, 37, 40, 42, 45, 49, or 50 more) new leaves than a corresponding control plant. In other cases, when a polypeptide described herein is expressed in a transgenic plant, the transgenic plant can exhibit a seed number (number of seeds per plant) from about 10% to about 95% greater (e.g., from about 10% to about 20%; from about 10% to about 50%; from about 10% to about 70%; from about 20% to about 60%; from about 20% to about 75%; from about 25% to about 85%; from about 30% to about 70%; from about 35% to about 90%; from about 40% to about 60%; from about 40% to about 85%; from about 50% to about 80%; from about 50% to about 90%; or from about 70% to about 90% greater) than a control plant not expressing the polypeptide. In certain cases, when a polypeptide described herein is expressed in a transgenic plant, the transgenic plant can exhibit an increase in seed weight per plant from about 5% to about 20% greater (e.g., from about 5% to about 10%; from about 8% to about 12%; from about 10% to about 15%; from about 8% to about 18% greater) than the seed weight in a plant not expressing the polypeptide.

Transgenic plants also may exhibit a lower transpiration rate compared to control plants of the same genetic background. Transpiration rate is another physiological parameter that is indicative of how well a plant can tolerate drought conditions. For example, plants with a low transpiration rate are expected to lose water more slowly than plants with higher transpiration rates and therefore would be expected to better withstand drought conditions (i.e., have better drought tolerance). When a polypeptide described herein is expressed in a transgenic plant, the transgenic plant can exhibit a transpiration rate that is reduced by about 1 to 100% (e.g., 2%, 4%, 6%, 8%, 10%, 12%, 15%, 18%, 22%, 28%, 35%, 37%, 42%, 45%, 47%, 50%, 55%, 64%, 68%, 71%, 75%, 77%, 80%, 83%, 86%, 89%, 90%, 92%, 95%, 98%, or 99%) as compared to the transpiration rate in a corresponding control plant.

It should be noted that phenotypic effects typically are evaluated for statistical significance by analysis of one or more experiments. It is understood that when comparing phenotypes to assess the effects of a polypeptide, a difference in phenotypes is considered statistically significant at $p \leq 0.05$ with an appropriate parametric or non-parametric statistic, e.g., Chi-square test, Student's t-test, Mann-Whitney test, or F-test. Other phenotypic effects can be evaluated by methods known to those of ordinary skill in the art, including cell length measurements at specific times in development, counting of new shoots, and determining new leaf numbers.

Typically, a difference between the growth rate, drought recovery, and/or transpiration rate in seeds of a transgenic plant relative to seeds of a corresponding control plant is considered statistically significant at $p \leq 0.05$ with an appropriate parametric or non-parametric statistic, e.g., Chi-square test, Student's t-test, Mann-Whitney test, or F-test. In some embodiments, a difference in growth rate, drought recovery, and/or transpiration rate is statistically significant at $p<0.01$, $p<0.005$, or $p<0.001$. A statistically significant difference in, for example, the growth rate, drought recovery, and/or transpiration rate in seeds of a transgenic plant compared to the content in seeds of a corresponding control plant indicates that (1) the recombinant nucleic acid present in the transgenic plant alters the growth rate, drought recovery, and/or transpiration rate in seeds and/or (2) the recombinant nucleic acid warrants further study as a candidate for altering the carbon content in a plant.

Articles of Manufacture

Also provided herein are articles of manufacture that can include, for example, a mixture of seeds (e.g., a substantially uniform mixture of seeds) from the transgenic plants provided herein. The seed mixture can be conditioned and packaged using means known in the art to prepare an article of manufacture. A package of seed can have a label e.g., a tag or label secured to the packaging material, a label printed on the packaging material or a label inserted within the package. The label can indicate that plants grown from the seeds contained within the package can produce a crop having a greater rate of growth under drought conditions, enhanced drought-recovery, and/or a lower transpiration rate relative to corresponding control plants.

The invention is further described in the following examples, which do not limit the scope of the invention described in the claims.

EXAMPLES

Example 1

Materials and Methods

Sequence searches: Query nucleic acid and amino acid sequences were searched against subject nucleic acid or amino acid sequences residing in public or proprietary databases. Such searches were done using the Washington University Basic Local Alignment Search Tool Version 2.0 (WU-Blast2) program. The WU-Blast2 program is available online from Washington University at blast.wustl.edu. Instructions explaining how to use the program also are available online at blast.wustl.edu/blast/README. A list of general and specialized sequence search services that run WU-Blast2 also is available online from Washington University (blast.wustl.edu). A WU-Blast2 service for *Arabidopsis* can be found on the World Wide Web at arabidopsis.org/wublast/index2. Unless otherwise noted, the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to $10^{-5}$, the Number of best alignments to show was set to "10000," and the "Sort output" option was set to sort the output by "pvalue." The option "-postsw" was turned on to optimize the sequence alignment using the Smith-Waterman algorithm.

Construction of transformation vector: Two constructs were used for transformation. The promoter-less pNB4-NCED3 plasmid was used to generate control plants. The pNB4_p35S:AtNCED3 plasmid, in which the p35S promoter was operably linked to the *Arabidopsis* NCED3 cDNA cloned from ecotype WS (FIG. 2A; SEQ ID NO:1), was used to generate test plants. To make these constructs, an NCED3 cDNA fragment was amplified from WS cDNA by PCR using the following primers: AtNCED3_5' (5'-CCGGAAGCTTCTGATTGAACACACT-TGAAAAATGGCTT; SEQ ID NO:4), and AtNCED3_3' (5'-GCAGTCTAGACACATAAGAACTCACAC-GACCTGCTT; SEQ ID NO:5). The resulting NCED3 cDNA PCR fragments were digested with Hind III and Xba I, and sub-cloned into the pNB4-UAS-NOS vector backbone to give rise to pNB4_NCED3, the control construct. Alternatively, the resulting NCED3 cDNA PCR fragments were digested HindIII and XbaI, and sub-cloned into the pNB4-35S vector backbone to give rise to pNB4_P35S:NCED3, the test construct. The pNB4_NCED3 and pNB4_P35S:NCED3 constructs each contained the left and right borders of Agrobacterium, a spectinomycin-resistance gene for selection in bacteria, and the BAR gene for selection of resistance in plants.

Plant material and transformation: The rice cultivar Kitaake was used for all experiments. Transformation was done using transformation-competent callus cells and an *Agrobacterium*-mediated process. Kitaake was developed in Hokkaido (Japan) for cold tolerance, but is not adapted to any kind of moisture or drought environment.

The pNB4-NCED3 and pNB4_PS35:NCED3 constructs were introduced into rice plants in parallel using *Agrobacterium* and transformation-competent callus. Callus induction, transformation, selection of transformed cells and plant regeneration were done in parallel for plant material containing each construct. The control, or promoter-less construct, pNB4-NCED3, was used for transformation and generation of control plants. pNB4_P35S:NCED3 was used for transformation and generation of test plants.

RT-PCR: To screen for transformants and genotype plants, about 120 mg of young leaf material was collected from transgenic rice plants, and total RNA was isolated using a Qiagen RNeasy Plant mini kit (Qiagen Inc., Valencia, Calif.). RNA samples were treated with DNase I, MseI, and DdeI before reverse transcription to eliminate genomic DNA contamination. The first strand cDNA was made by reverse transcription of 1 μg total RNA using Superscript II Reverse Transcriptase (Invitrogen Life Technology, Carlsbad, Calif.) in 20 μL. One μL cDNA was used for PCR with Platinum Taq DNA polymerase (Invitrogen Life Technology). PCR reactions were performed with a GeneAmp PCR System 9700 thermocycler (PE Applied Biosystems, Foster City, Calif.) at 95° C. for 5 minutes, denaturing at 94° C. for 1 minute, annealing at 52° C. for 1 minute, and extension at 72° C. for 1 minute cycles with a final extension at 72° C. for 7 minutes. NCED3 sequences were amplified using the 3' end primer NCED3Se4 (5'-CCGTCCGATCATCTC-CAACGAA; SEQ ID NO:6) and the 5' end primer pNB4Seq3' (5'-GTTGCCGGTCTTGCGATGAT; SEQ ID NO:7). Rice tubulin was used as an internal control, and was amplified using the primers 5'-ACCCTATGGCCAGATCTT (rtublf; SEQ ID NO:8) and 5'-CAGCTTGAGAGTCCT-GAAG (rtublr; SEQ ID NO:9). BaR-specific primers were used to detect the presence of the BaR gene. The pNB4_p35S:AtNCED3 plasmid was used as a positive control, and RNA from non-transgenic plants was used as a negative control. Seventeen test plants (i.e., transformed with pNB4_p35S:AtNCED3) were genotyped. Of these, fourteen were shown to contain the *Arabidopsis* NCED3 sequence. Thus, transformation of rice plants with pNB4_p35S:AtNCED3 was successful.

Regeneration of $R_1$ plants: Cells and plants that directly resulted from the transformation and regeneration were designated $R_1$ plants. No significant differences were observed in the transformation or the regeneration frequencies between the two constructs. $R_1$ seeds were sterilized and germinated on Murashige & Skoog (MS) medium containing 15 mg/L of the antibiotic Bialaphos (Apollo Scientific Ltd, Bredbury, United Kingdom) to select for transformed plants. All plants were kept in a Percival (Perry, Iowa) growth chamber operating at 28° C. and a 16 h:8 h light:dark cycle.

$GA_3$ treatment: $R_2$ seeds were surface-sterilized with 20% bleach and germinated on half-strength MS containing 0.4 mL/L Finale and filter-sterilized GA3 (gibberellin) to final concentrations of 0, 10, 100, 250, 500 or 1,000 μM.

Measurement of transpiration rate: For line T13, $R_2$ seeds were germinated 2 weeks prior to wild-type seeds in order to have similar-sized $R_2$ and control seedlings. T7 and T9 $R_2$ seeds and wild-type control seeds were germinated and established at the same time. Plants were transferred to a 15 mL Corning tube containing half-strength MS salts but no sugar, and the final volume of the growth medium was adjusted to 14 mL. The tubes were wrapped tightly with several layers of Parafilm® to ensure that the only water loss occurred by transpiration. The $R_2$ and wild-type seedlings were positioned randomly relative to each other and were grown at 28° C., 16 h:8 h light:dark cycle.

The water level was recorded after 95 and 120 hours for each seedling. Roots were removed and the remaining green parts of the seedlings were weighed so that fresh weight (FW) measurements could be determined. The transpiration rate for each seedling was calculated using the following equation, where FW is fresh weight:

$$\text{Transpiration rate (mL/100 mg } FW/\text{day)} = \frac{\text{Water loss (mL) in 95 or 120 hrs}}{FW(\text{mg})} \times 100 \times 24/95 \text{ or } 120$$

Example 2

Growth Phenotypes $R_1$ test plants containing the pNB4_p35S:AtNCED3 construct showed a range of sizes. Approximately half of the test plants were smaller than control plants; in general, these test plants were slower growing than controls containing the pNB4_AtNCED3 construct. The other test plants did not exhibit apparent size aberrations and seemed to grow at a rate similar to control plants. The size difference within the test plants may be due to different levels of transgene expression, which in turn may be due to the different genomic positions the NCED3 transgene occupies in the different lines. It is also possible that the increased ABA levels resulting from the overexpression of NCED3 could account for a slightly impaired growth under normal conditions.

Example 3

Drought Phenotypes of $R_1$ Plants

Ten pairs of $R_1$ plants, each pair consisting of one control plant (containing pNB4_AtNCED3) and one test plant (containing pNB4_p35S:AtNCED3) were transplanted to pots containing soil. The plants in each pair were matched by size. Plants were allowed to grow in soil for 18 days before being subjected to drought treatment, which was carried out by withholding water for 8 or for 10 days. For pairs of plants that showed evidence of phenotype after 8 days, water was added to revive plants. For the others, water was added after 10 days. Drought symptoms the recovery therefrom were assessed by visual observation.

Of the 10 pairs of plants, three pairs failed to show clearly defined symptoms following a 10-day drought treatment. The comparisons between control and test plants with regard to drought symptoms and drought recovery were optimized when using pairs of plants grown side-by-side in single pots, since results from growing control and test plants in separate pots may be skewed due to pot-to-pot experimental variations.

Two kinds of responses were observed under drought conditions. In the first, plants carrying the pNB4_p35S: AtNCED3 construct (e.g., plants in lines T13 and T16) showed more vigorous and robust growth than control lines carrying the pNB4_AtNCED3 construct (e.g., plants in lines C12 and C13). Following 10 days of drought, the test plants expressing the NCED3 transgene were larger and more robust than the control plants.

Figure 4:
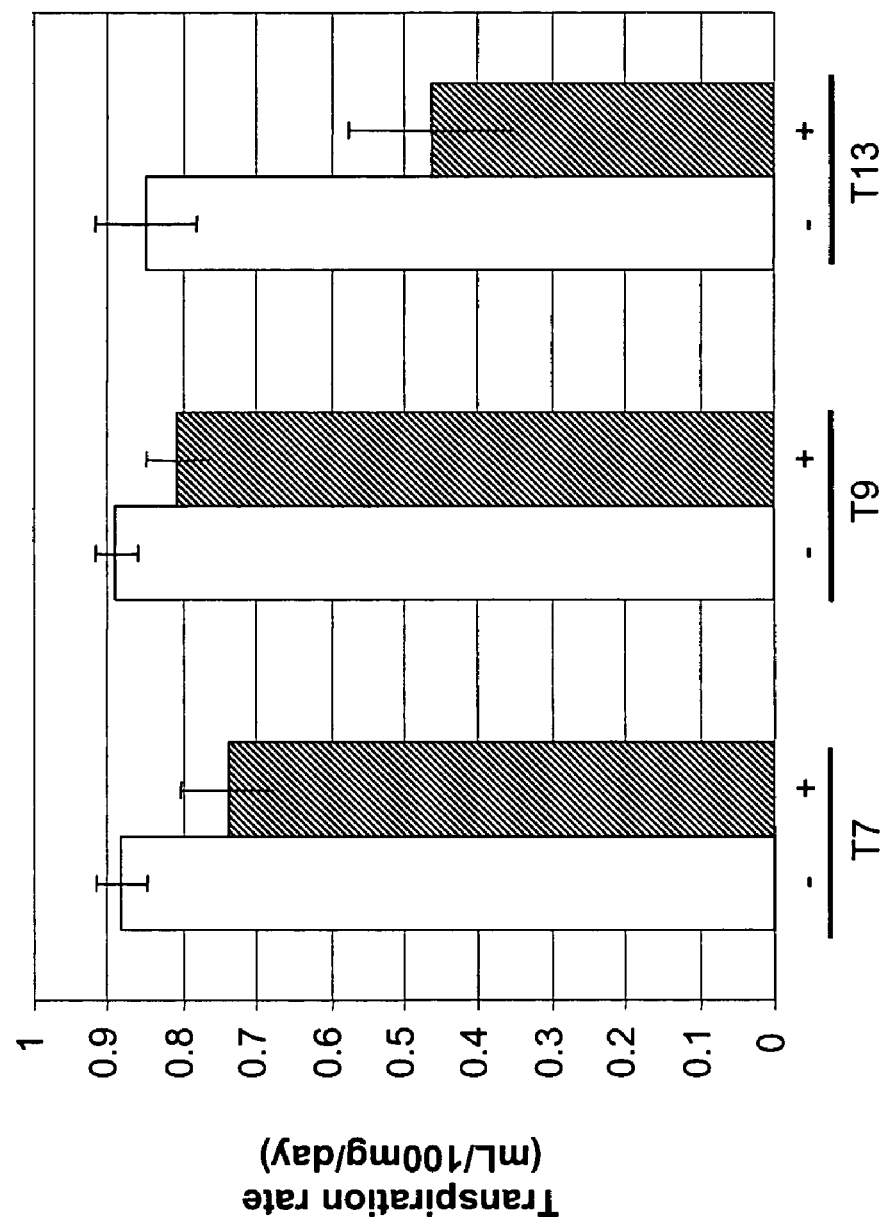
FIG. 4 is a graph illustrating a comparison of transpiration rates between $R_2$ seedlings that show evidence of presence or absence of expression of transgenic NCED3.

In the second type of response, test plants (e.g., plant lines T2, T6, T7, T9 and T15) showed better recovery following the drought treatment as compared to control plant lines C7, C8, C9, C10 and C15. The results of the drought recovery experiment are shown in FIG. 4. For the control plants, the phenotype during the drought treatment was not obviously different from that of the test plants, and only became apparent when the plants had been re-watered and were in the recovery phase.

Taken together, these data suggest that the *Arabidopsis* NCED3 gene can enhance the tolerance of rice plants to drought, and that the enhanced tolerance to drought can take the form of enhanced growth under drought or improved recovery following drought. Both of these phenotypes could be valuable in other crops such as corn, wheat, barley, oats, or millet, which can experience intermittent drought.

Example 4

Germination Phenotypes

Seeds were collected from 11 $R_1$ lines containing the pNB4_p35S:AtNCED3 construct, including 2 lines (T8 and T10) that were not assayed as pairs with controls on soil and one line (T11) that had not shown clear symptoms. The collected seeds were assayed for their germination phenotype. Seeds from test lines T13 and T16, which showed improved drought tolerance in the $R_1$ generation, germinated 7 to 10 days later and grew more slowly than the control line T3 (a PCR-negative line for the NCED3 transgene). Seeds from test lines T2, T6, T7 and T9, which showed improved recovery following a drought treatment, germinated 1 or 2 days later and grew slightly slower than the control. Line T7 segregated some albino seedlings, which can occur when rice plants are subjected to tissue culture conditions. Seeds also were germinated from test lines T13 and T16 in the absence of Bialophos, and clear segregation of normal and late germination phenotypes was observed, consistent with the view that the excess ABA induced by the transgene may be responsible for the germination delay. Seeds from the test line T15 also showed a slow growth on Bialophos, but there was no clear segregation of the phenotype in the absence of Bialophos, suggesting that the BaR gene conferred only partial resistance in this line.

To test the germination capacity of $R_3$ generation seeds, homozygous $R_3$ seeds of lines T6 and T7 were germinated on MS medium containing Finale. Out of the five groups of $R_2$ plants that descended from T6, T6-1 and T6-4 $R_2$ plants failed to show evidence of segregation in the $R_3$ generation. Out of the five groups of the $R_2$ plants that descended from T7, the T7-5 $R_2$ plants did show an evidence of segregation in the $R_3$ generation. Germination in both the T6-1 and T7-5 $R_3$ populations was slightly delayed as compared to the wild-type control. These results suggest that increased ABA levels can result in a slight delay in germination.

Taken together, the data suggest that expression of the NCED3 transgene may prolong seed dormancy and may impair growth under normal environmental conditions. However, although some $R_1$ test plants were developmentally impaired under normal conditions, they reached or surpassed in size the $R_1$ control plants when both control and test plants were subjected to a drought treatment. $R_1$ test plants also surpassed in size the $R_1$ control plants when these two groups of plants were subjected to a drought-recovery treatment.

Example 5

Transgene Expression

Semi-quantitative RT-PCR was performed with $R_2$ plant material for lines T3, T6, T7, T13 and T16. All of the $R_2$ plants showed expression of the NCED3 transgene except for line T3, which exhibited a much weaker band by RT-PCR. Detecting the presence of the NCED3 transgene by RT-PCR was met with difficulty for T3 and any of its progeny when utilizing primers that spanned the 3' region of 35S and 5' region of NCED3. One possibility is that there was a deletion in the 3' region of the 35S promoter, thus resulting in reduced expression of NCED3, as evidenced by RT-PCR.

Intense RT-PCR bands demonstrating expression of the NCED3 transgene were detected for lines T6 and T7. These RT-PCR results were consistent with the better recovery following a drought treatment exhibited by lines T6 and T7. Consistency between the presence of intense RT-PCR bands and improved drought tolerance also was exhibited by lines T13 and T16. Taken together, these data suggest that lines exhibiting expression of the NCED3 transgene have a greater rate of growth under drought conditions and are better able to recover following a drought treatment as compared to control plants.

Example 6

Effects of $GA_3$ Treatment

ABA and $GA_3$ (gibberellin) can act antagonistically in seed germination. To determine whether $GA_3$ could release the prolonged dormancy evident in the NCED3 transgenic seeds, $GA_3$ was added to the growth medium on which the seeds were placed for germination. Even at a concentration as low as 10 µM, $GA_3$ accelerated germination. Higher concentrations of $GA_3$ did not significantly improve seed germination, although the resulting seedlings were more elongated. Thus, addition of exogenous of $GA_3$ can, at least in part, overcome the off-type of prolonged dormancy.

Example 7

Measurement of Transpiration Rates

The opening and closing of the stomata and the associated transpiration rate are important determinants of drought tolerance. To measure and compare the transpiration rates of test and control plants, $R_2$ seeds were germinated 2 weeks prior to wild-type seeds in order to have similar-sized $R_2$ and control seedlings. Plants were transferred to 15 mL Corning tubes (Acton, Mass.) containing half-strength of MS salts, but without any sugar, and the final volume of the growth medium was adjusted to 14 mL. The tubes were wrapped tightly with several layers of Parafilm M® to ensure that the only water loss that occurred was by transpiration. The $R_2$ and wild-type seedlings were positioned randomly relative to each other, and the water level was recorded after 95 and 120 hours for each seedling. Roots were then removed and the remaining green parts of the seedlings were weighed so that fresh weight measurements could be determined and transpiration rates could be calculated using the equation provided in Example 1.

Transpiration rates were compared for lines T7, T9 and T13, between their PCR-positive and PCR-negative segregants, and to wild-type segregant seedlings. As shown in FIG. 4, plants expressing NCED3 consistently showed lower transpiration rates than their corresponding PCR-negative controls. Line T13, which was among the lines showing a greater rate of growth under drought conditions, exhibited the lowest transpiration rate, reduced by up to about 50% in its $R_2$ plants relative to wild-type segregants. These data suggest that the improved response of NCED3-expressing plants to a drought treatment results at least in part from a reduction of the plant transpiration rate, which presumably resulted from increased concentrations of ABA in the NCED3-expressing plants.

Example 8

Drought Tolerance of $R_2$ Plants

To confirm that the increase in drought tolerance conferred by Arabidopsis NCED3 expression in rice is heritable, dehydration experiments were performed in R₂ plants. Two R₂ plants were grown for each of the T13 and T16 lines. Plants T13-26 and T13-27 were descendants of line T13, and plants T16-23 and T16-24 were descendants of line T16. Each pot contained an R₂ NCED3-expressing plant and an untransformed wild-type control, such that a pair of plants was in a single pot and the dehydration conditions were uniform for the two plants. The dehydration treatment started 17 days following transplantation to soil, by removing any surplus water and stopping watering thereafter. Photographs were taken at 4 time-points: at the start of dehydration (referred to as D0), at day 11 (D11), at the end of the dehydration (D15, D16, and D17) and 4 hours after re-watering (D15-4 h, D16-4 h, and D17-4 h). The timing of re-watering depended on the severity of the leaf symptoms. Water loss was observed to be faster from pots containing the largest plants.

All of the R₂ plants exhibited drought tolerance during dehydration and a quick recovery following re-watering. It was observed that although plants T13-26 and T13-27 were smaller in size than control plants at the start of dehydration (D0), they were as tall as the control plants following the drought treatment (D16 and D17). In addition, when re-watered, the transgenic plants recovered fully in less than 4 hours, whereas the control plants showed little or no recovery within this time frame. Taken together, the data suggest that the *Arabidopsis* NCED3 gene enhances the tolerance of rice plants to drought stress, and that this enhanced tolerance to drought stress is heritable. Again, enhanced tolerance to drought was observed to take the form of enhanced growth under drought and/or improved recovery following drought.

The performance of test transgenic rice plants under a severe drought treatment also was investigated. An R₂ descendant of line T16 (T16-5) was grown alongside an untransformed wild-type control plant. Both plants were dehydrated for 7 days starting 24 days following transplantation to soil, and then re-watered for 5 consecutive days. The T16-5 tansgenic plant survived this extreme dehydration, whereas the wild-type control did not recover within the 5-day time frame. In the control plant, the apical one-third of the leaves dried up and shriveled within 90 days. In the T16-5 plant, there was no reduction in seed set or fertility. Further studies showed that homozygous plants of lines T6 and T7 had an even better recovery from drought than R₁ plants. Taken together, these data confirm the R₁ results, and indicate that rice plants expressing the *Arabidopsis* NCED3 transgene have an enhanced drought tolerance that is heritable.

It is noted that although expression of the *Arabidopsis* NCED3 transgene can cause delayed germination and growth, the T13 and T16 plants were all able catch up with and surpass wild-type controls when maintained under drought or allowed to recover from drought, and the plant yield was not affected by this delay. In fact, although T13 and T16 plants were slightly shorter than wild-type controls under normal growth and watering conditions, these transgenic plants had a yield that was better than that of control plants under drought conditions.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic plant comprising an exogenous nucleic acid, said exogenous nucleic acid comprising a nucleotide sequence that encodes the polypeptide having the amino acid sequence set forth in SEQ ID NO:2.

2. The transgenic plant of claim 1, wherein said plant exhibits a greater rate of growth under drought conditions relative to a corresponding plant of the same genetic background that lacks the nucleotide sequence encoding said polypeptide.

3. The transgenic plant of claim 1, wherein said plant exhibits enhanced drought-recovery relative to a corresponding plant of the same genetic background that lacks the nucleotide sequence encoding said polypeptide.

4. The transgenic plant of claim 1, wherein said plant exhibits a lower transpiration rate relative to a corresponding plant of the same genetic background that lacks the nucleotide sequence encoding said polypeptide.

5. The transgenic plant of claim 1, wherein said polypeptide is a dicotyledonous 9-cis-epoxycarotenoid dioxygenase.

6. The transgenic plant of claim 1, wherein said plant is hemizygous for said exogenous nucleic acid.

7. The transgenic plant of claim 1, wherein said plant is homozygous for said exogenous nucleic acid.

8. The transgenic plant of claim 1, wherein said plant is an F1 plant, F2 plant, BC1 plant, or BC2 plant, and wherein said F1 plant, F2 plant, BC1 plant or BC2 plant comprises said exogenous nucleic acid.

9. The transgenic plant of claim 1, wherein said plant is fertile.

10. The transgenic plant of claim 1, wherein said plant is dicotyledonous.

11. The transgenic plant of claim 1, wherein said plant is monocotyledonous.

12. The transgenic plant of claim 11, wherein said plant is corn, wheat, rye, barley, oat, rice, millet, sorghum, Kentucky bluegrass, bluestem, weeping lovegrass, switchgrass, or fescue.

13. A seed of the transgenic plant of claim 1, wherein said seed comprises said exogenous nucleic acid.

* * * * *

SEQUENCE LISTING

<160> NUMBER OF SEQ ID NOS: 9

<210> SEQ ID NO 1
<211> LENGTH: 1800
<212> TYPE: DNA
<213> ORGANISM: Arabidopsis thaliana

<400> SEQUENCE: 1

```
atggcttctt tcacggcaac ggctgcggtt tctgggagat ggcttggtgg cgatcatact      60
cagccgccat tatcgtcttc tcaaagctcc gacttgagtt attgtagctc cttacctatg     120
gccggtcgtg tcacacgtaa gctcaatgtt tcatctgcgc ttcacactcc tccagctctt     180
catttcccta agcaatcatc aaactctccc gccattgttg ttaagcccaa agccaaagaa     240
tccaacaata aacagatgaa tttgttccag agagcggcgg cggcagcgtt ggacgcggcg     300
gagggtttcc ttgtcagcca cgagaagcta cacccgcttc ctaaaacggc tgatcctagt     360
gttcagatcg ccggaaattt tgctccggtg aatgaacagc ccgtccggcg taatcttccg     420
gtggtcggaa aaattcccga ttccatcaaa ggagtgtatg tgcgcaacgg agctaaccca     480
cttcacgagc cggtgacagg tcaccacttc ttcgacggag acggtatggt tcacgccgtc     540
aaattcgaag acgttcagc tagctacgct tgccggttca ctcagactaa ccggtttgtt     600
caggaacgtc aattgggtcg accggttttc cccaaagcca tcggtgagct tcacggacac     660
accggtattg cccggctcat gctattctac gccagagctg cagccggtat agtcggcccg     720
```

```
gcacacggaa ccggtgtggc caacgccggt ttggtctatt tcaacggccg gttattggct    780
atgtcggagg atgatttacc ttaccaagtt cggatcactc ccaatggaga tttaaaaacc    840
gttggtcggt tcaattttga tggacaatta gaatccacaa tgattgccca cccgaaagtc    900
gacccggaat ccggtgaact cttcgcttta agctacgacg tcgtttcaaa gccttaccta    960
aaatacttcc gattctcacc ggacggaact aaatcaccgg acgtcgagat tcagcttgat   1020
cagccaacga tgatgcacga tttcgcgatt acagagaact tcgtcgtcgt acctgaccag   1080
caagtcgttt tcaagctgcc ggagatgatc cgcggtgggt ctccggtggt ttacgacaag   1140
aacaaggtcg caagattcgg gattttagac aaatacgccg aagattcatc gaacattaag   1200
tggattgatg ctccagattg cttctgcttc catctctgga acgcttggga agagccagaa   1260
acagatgaag tcgtcgtgat agggtcctgt atgactccac cagactcaat tttcaacgag   1320
tctgacgaga atctcaaggg tgtcctgtct gaaatccgcc tgaatctcaa accggtgaa    1380
tcaactcgcc gtccgatcat ctccaacgaa gatcaacaag tcaacctcga agcagggatg   1440
gtcaacagaa acgtgcttgg ccgtaaaacc aaattcgctt acttggcttt agccgagccg   1500
tggcctaaag tctcaggatt cgctaaagtt gatctcacta ctggagaagt taagaaacat   1560
ctttacggcg ataaccgtta cggaggagag cctctgtttc tccccggaga aggaggagag   1620
gaagacgaag gatacatcct ctgtttcgtt cacgacgaga agacatggaa atcggagtta   1680
cagatagtta acgccgttag cttagaggtt gaagcaacgg ttaaacttcc gtcaagggtt   1740
ccgtacggat ttcacggtac attcatcgga gccgatgatt tggcgaagca ggtcgtgtga   1800
```

<210> SEQ ID NO 2
<211> LENGTH: 599
<212> TYPE: PRT
<213> ORGANISM: Arabidopsis thaliana

<400> SEQUENCE: 2

```
Met Ala Ser Phe Thr Ala Thr Ala Ala Val Ser Gly Arg Trp Leu Gly
 1               5                  10                  15

Gly Asp His Thr Gln Pro Pro Leu Ser Ser Gln Ser Ser Asp Leu
            20                  25                  30

Ser Tyr Cys Ser Ser Leu Pro Met Ala Gly Arg Val Thr Arg Lys Leu
        35                  40                  45

Asn Val Ser Ser Ala Leu His Thr Pro Pro Ala Leu His Phe Pro Lys
    50                  55                  60

Gln Ser Ser Asn Ser Pro Ala Ile Val Val Lys Pro Lys Ala Lys Glu
65                  70                  75                  80

Ser Asn Asn Lys Gln Met Asn Leu Phe Gln Arg Ala Ala Ala Ala
                85                  90                  95

Leu Asp Ala Ala Glu Gly Phe Leu Val Ser His Glu Lys Leu His Pro
            100                 105                 110

Leu Pro Lys Thr Ala Asp Pro Ser Val Gln Ile Ala Gly Asn Phe Ala
        115                 120                 125

Pro Val Asn Glu Gln Pro Val Arg Arg Asn Leu Pro Val Val Gly Lys
    130                 135                 140

Ile Pro Asp Ser Ile Lys Gly Val Tyr Val Arg Asn Gly Ala Asn Pro
145                 150                 155                 160

Leu His Glu Pro Val Thr Gly His His Phe Phe Asp Gly Asp Gly Met
                165                 170                 175

Val His Ala Val Lys Phe Glu Asp Gly Ser Ala Ser Tyr Ala Cys Arg
```

```
            180                 185                 190
Phe Thr Gln Thr Asn Arg Phe Val Gln Glu Arg Gln Leu Gly Arg Pro
        195                 200                 205
Val Phe Pro Lys Ala Ile Gly Glu Leu His Gly His Thr Gly Ile Ala
210                 215                 220
Arg Leu Met Leu Phe Tyr Ala Arg Ala Ala Gly Ile Val Gly Pro
225                 230                 235                 240
Ala His Gly Thr Gly Val Ala Asn Ala Gly Leu Val Tyr Phe Asn Gly
                245                 250                 255
Arg Leu Leu Ala Met Ser Glu Asp Leu Pro Tyr Gln Val Arg Ile
        260                 265                 270
Thr Pro Asn Gly Asp Leu Lys Thr Val Gly Arg Phe Asn Phe Asp Gly
        275                 280                 285
Gln Leu Glu Ser Thr Met Ile Ala His Pro Lys Val Asp Pro Glu Ser
        290                 295                 300
Gly Glu Leu Phe Ala Leu Ser Tyr Asp Val Val Ser Lys Pro Tyr Leu
305                 310                 315                 320
Lys Tyr Phe Arg Phe Ser Pro Asp Gly Thr Lys Ser Pro Asp Val Glu
                325                 330                 335
Ile Gln Leu Asp Gln Pro Thr Met Met His Asp Phe Ala Ile Thr Glu
                340                 345                 350
Asn Phe Val Val Pro Asp Gln Gln Val Val Phe Lys Leu Pro Glu
        355                 360                 365
Met Ile Arg Gly Gly Ser Pro Val Val Tyr Asp Lys Asn Lys Val Ala
        370                 375                 380
Arg Phe Gly Ile Leu Asp Lys Tyr Ala Glu Asp Ser Ser Asn Ile Lys
385                 390                 395                 400
Trp Ile Asp Ala Pro Asp Cys Phe Cys Phe His Leu Trp Asn Ala Trp
                405                 410                 415
Glu Glu Pro Glu Thr Asp Glu Val Val Ile Gly Ser Cys Met Thr
                420                 425                 430
Pro Pro Asp Ser Ile Phe Asn Glu Ser Asp Glu Asn Leu Lys Gly Val
        435                 440                 445
Leu Ser Glu Ile Arg Leu Asn Leu Lys Thr Gly Glu Ser Thr Arg Arg
450                 455                 460
Pro Ile Ile Ser Asn Glu Asp Gln Gln Val Asn Leu Glu Ala Gly Met
465                 470                 475                 480
Val Asn Arg Asn Val Leu Gly Arg Lys Thr Lys Phe Ala Tyr Leu Ala
                485                 490                 495
Leu Ala Glu Pro Trp Pro Lys Val Ser Gly Phe Ala Lys Val Asp Leu
        500                 505                 510
Thr Thr Gly Glu Val Lys Lys His Leu Tyr Gly Asp Asn Arg Tyr Gly
        515                 520                 525
Gly Glu Pro Leu Phe Leu Pro Gly Glu Gly Gly Glu Asp Glu Gly
        530                 535                 540
Tyr Ile Leu Cys Phe Val His Asp Glu Lys Thr Trp Lys Ser Glu Leu
545                 550                 555                 560
Gln Ile Val Asn Ala Val Ser Leu Glu Val Glu Ala Thr Val Lys Leu
                565                 570                 575
Pro Ser Arg Val Pro Tyr Gly Phe His Gly Thr Phe Ile Gly Ala Asp
        580                 585                 590
Asp Leu Ala Lys Gln Val Val
        595
```

<210> SEQ ID NO 3
<211> LENGTH: 583
<212> TYPE: PRT
<213> ORGANISM: Artificial Sequence
<220> FEATURE:
<223> OTHER INFORMATION: Consensus

<400> SEQUENCE: 3

```
Met Ala Thr Thr Ala Ala Ser Asn Thr Trp Ile Gly Gly Asn Leu
 1               5                  10                  15

Pro Pro Pro Leu Ser Ser Ser Ser Ser Leu Leu Ser Tyr Cys Ser
             20                  25                  30

Ser Ser Ser Ser Ser Thr Ile Thr Arg Ser Leu Gln Val Pro Leu His
             35                  40                  45

Thr Pro Ala Leu Gln Ser Pro Lys Gln Ser Ser Thr Ser Pro Ala Ile
         50                  55                  60

Val Val Pro Thr Gln Ala Thr Pro Ser Asn Ser Lys Trp Asn Leu Phe
 65                  70                  75                  80

Gln Arg Ala Ala Ala Ala Leu Asp Ala Val Glu Gly Ala Leu Val
                 85                  90                  95

Ser His Glu Leu Glu His Pro Leu Pro Lys Thr Ala Asp Pro Arg Val
                100                 105                 110

Gln Ile Ala Gly Asn Phe Ala Pro Val Pro Glu His Pro Val Arg Gln
            115                 120                 125

Asn Leu Pro Val Val Gly Lys Ile Pro Lys Cys Ile Asp Gly Val Tyr
    130                 135                 140

Val Arg Asn Gly Ala Asn Pro Leu Phe Glu Pro Val Ala Gly His His
145                 150                 155                 160

Phe Phe Asp Gly Asp Gly Met Val His Ala Val Lys Phe Thr Asn Gly
                165                 170                 175

Ser Ala Ser Tyr Ala Cys Arg Phe Thr Glu Thr Asn Arg Leu Val Gln
            180                 185                 190

Glu Arg Ser Leu Gly Arg Pro Val Phe Pro Lys Ala Ile Gly Glu Leu
        195                 200                 205

His Gly His Ser Gly Ile Ala Arg Leu Met Leu Phe Tyr Ala Arg Gly
    210                 215                 220

Leu Phe Gly Leu Val Asp Gly Ser His Gly Thr Gly Val Ala Asn Ala
225                 230                 235                 240

Gly Leu Val Tyr Phe Asn Gly Arg Leu Leu Ala Met Ser Glu Asp Asp
                245                 250                 255

Leu Pro Tyr His Val Arg Ile Thr Pro Asn Gly Asp Leu Lys Thr Val
            260                 265                 270

Gly Arg Phe Asp Phe Asp Gly Gln Leu Glu Ser Thr Met Ile Ala His
        275                 280                 285

Pro Lys Leu Asp Pro Val Ser Gly Glu Leu Phe Ala Leu Ser Tyr Asp
    290                 295                 300

Val Val Gln Lys Pro Tyr Leu Lys Tyr Phe Arg Phe Ser Pro Asp Gly
305                 310                 315                 320

Thr Lys Ser Pro Asp Val Glu Ile Pro Leu Asp Gln Pro Thr Met Met
                325                 330                 335

His Asp Phe Ala Ile Thr Glu Asn Phe Val Val Pro Asp Gln Gln
            340                 345                 350

Val Val Phe Lys Leu Pro Glu Met Ile Arg Gly Gly Ser Pro Val Val
        355                 360                 365
```

-continued

```
Tyr Asp Lys Asn Lys Val Ser Arg Phe Gly Ile Leu Asp Lys Tyr Ala
    370                 375                 380

Lys Asp Ala Ser Glu Met Lys Trp Ile Asp Ala Pro Asp Cys Phe Cys
385                 390                 395                 400

Phe His Leu Trp Asn Ala Trp Glu Glu Pro Glu Thr Asp Glu Val Val
                405                 410                 415

Val Ile Gly Ser Cys Met Thr Pro Pro Asp Ser Ile Phe Asn Glu Ser
            420                 425                 430

Asp Glu Ser Leu Lys Ser Val Leu Ser Glu Ile Arg Leu Asn Leu Lys
            435                 440                 445

Thr Gly Glu Ser Thr Arg Arg Pro Ile Ile Ser Asp Asp Glu Gln Val
    450                 455                 460

Asn Leu Glu Ala Gly Met Val Asn Arg Asn Lys Leu Gly Arg Lys Thr
465                 470                 475                 480

Gln Phe Ala Tyr Leu Ala Leu Ala Glu Pro Trp Pro Lys Val Ser Gly
                485                 490                 495

Phe Ala Lys Val Asp Leu Thr Thr Gly Glu Val Lys Lys His Leu Tyr
            500                 505                 510

Gly Glu Asn Arg Phe Gly Gly Glu Pro Leu Phe Leu Pro Glu Gly Gly
            515                 520                 525

Glu Glu Asp Asp Gly Tyr Ile Leu Ala Phe Val His Asp Glu Lys Thr
530                 535                 540

Trp Lys Ser Glu Leu Gln Ile Val Asn Ala Val Asn Leu Lys Leu Glu
545                 550                 555                 560

Ala Thr Val Lys Leu Pro Ser Arg Val Pro Tyr Gly Phe His Gly Thr
                565                 570                 575

Phe Ile Ala Asp Leu Ala Gln
            580
```

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
ccggaagctt ctgattgaac acacttgaaa aatggctt                    38

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
gcagtctaga cacataagaa ctcacacgac ctgctt                      36

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ccgtccgatc atctccaacg aa                                     22

```
<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gttgccggtc ttgcgatgat                                                   20

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
accctatggc cagatctt                                                     18

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
cagcttgaga gtcctgaag                                                    19
```